United States Patent
Hocker

[11] Patent Number: 6,060,889
[45] Date of Patent: May 9, 2000

[54] SENSING WATER AND MOISTURE USING A DELAY LINE

[75] Inventor: Lon O. Hocker, Falmouth, Mass.

[73] Assignee: Onset Computer Corporation, Bourne, Mass.

[21] Appl. No.: 09/022,196

[22] Filed: Feb. 11, 1998

[51] Int. Cl.[7] .................................................. G01R 27/26
[52] U.S. Cl. ............................ 324/667; 324/640; 73/290
[58] Field of Search ................................ 324/76.54, 640, 324/649, 658, 663, 667, 674, 681; 331/65; 73/290 V

[56] References Cited

U.S. PATENT DOCUMENTS

| | | | |
|---|---|---|---|
| 2,607,830 | 8/1952 | Razek | 324/667 |
| 3,596,176 | 7/1971 | Laupman | 324/667 |
| 3,710,244 | 1/1973 | Rauchwerger | 324/61 R |
| 3,864,974 | 2/1975 | Rauchwerger | 73/304 C |
| 4,399,403 | 8/1983 | Strandberg | 324/58.5 |
| 4,560,923 | 12/1985 | Hanson | 324/61 QL |
| 4,616,425 | 10/1986 | Burns | 34/13.8 |
| 5,341,673 | 8/1994 | Burns et al. | 73/73 |
| 5,642,098 | 6/1997 | Maria et al. | 340/618 |
| 5,760,694 | 6/1998 | Nissim et al. | 340/604 |

*Primary Examiner*—Josie Ballato
*Assistant Examiner*—Vincent Q. Nguyen
*Attorney, Agent, or Firm*—Weingarten, Schurgin, Gagnebin & Hayes LLP

[57] ABSTRACT

A phase shift oscillator circuit having a delay line in a feedback loop is employed to determine soil moisture content and water level. The delay line is connected to the oscillator such that the dielectric value of the medium inside the delay line influences the frequency of the oscillator circuit. The delay line is placed in the medium to be studied. Soil moisture content and water level are calculated as a function of the frequency of the oscillator output, and changes in soil moisture content or water level are calculated as a function of changes in oscillator frequency over time. An elongated delay line is employed to measure water level.

31 Claims, 3 Drawing Sheets

SENSING WATER AND MOISTURE USING A DELAY LINE

CROSS REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

The present invention is generally related to sensors, and more particularly to an improved sensor for measuring soil moisture content and water level.

Apparatus and sensors for providing quantitative measurement of soil moisture and water level are known. Pressure actuated sensors known as "tensiometers" provide an indication of soil moisture content by employing a column of liquid within a closed generally cylindrically shaped container that is separated from the soil by a membrane. Relatively moist soil exerts little or no force on the tensiometer liquid. Relatively dry soil causes a reduction in pressure within the container, i.e., the pressure decreases within the container as the soil develops a greater capacity to soak up the tensiometer liquid. Soil moisture content is determined from the pressure exerted on the tensiometer liquid. However, data from tensiometers can be inaccurate and must be manually gathered and stored.

Relatively accurate electromechanical soil moisture sensors are also known. Soil exhibits a dielectric property which varies in proportion to moisture content. If the dielectric value of a region of soil can be measured, the moisture content of that region of soil can be calculated as a function of the measured dielectric value. Both time domain reflectomotry and capacitance measurement have been employed to determine the dielectric value of a region of soil to calculate moisture content.

In time domain reflectomotry a voltage pulse is transmitted through a length of transmission cable that terminates in the soil. A portion of the pulse is reflected at the cable/soil interface. The magnitude of the reflected portion of the pulse is indicative of the dielectric value of the soil. However, devices that employ time domain reflectomotry are relatively complex to implement and consequently tend to be costly to manufacture.

A capacitance based measurement may also be performed in which a soil "capacitor" is formed between two electrodes that are inserted into the soil. An excitation signal is applied to a circuit such as a Wein Bridge that includes the soil "capacitor" as the only component of unknown value. An output signal is produced in response to the excitation signal, and analysis of the output signal allows calculation of the capacitance value of the soil "capacitor." However, the apparant capacitance between the electrodes is affected by soil salinity which tends to introduce errors into soil moisture calculations when using a soil "capacitor."

Similar sensors are known for measuring water level, such as the level of water in a well. For example, it is known to calculate water level based on pressure. In a column of water, pressure increases as depth increases. Water pressure can be measured with a pressure sensor and employed to calculate water depth. However, variations in atmospheric pressure also affect pressure sensors. To compensate for variations in atmospheric pressure a separate sensor may be employed to measure atmospheric pressure and calculations may be based on differential pressure measurements. However, the equipment required for compensation increases the complexity of the apparatus and also increases the cost to manufacture such devices. It is also known to calculate water level by placing electrodes at opposite ends of a water column and determining the capacitance between the electrodes. However, the apparant capacitance between the electrodes is adversely influenced by the salinity of the water. Further, both types of water level measurement devices must be individually calculated to compensate for variations in construction.

BRIEF SUMMARY OF THE INVENTION

In accordance with the present invention, an oscillator circuit with a feedback loop delay line is employed to determine soil moisture content or water level. The feedback loop is connected to the oscillator such that the dielectric value of the medium inside the feedback loop directly influences the operating frequency of the oscillator circuit. When the medium inside the loop is soil, the amount of moisture in the soil influences a delay in the propagation of a feedback signal through the feedback loop. The feedback delay influences the operating frequency of the oscillator circuit. Soil moisture content values are calculated from the operating frequency of the oscillator circuit. When the medium inside the loop includes both air and water, the proportion of water to air influences the feedback delay because air and water have different dielectric values. Water level values may also calculated from the operating frequency of the oscillator circuit.

The oscillator circuit includes an inverting amplifier and a feedback loop. The feedback loop is placed in the soil to be analyzed and the amplifier output frequency is monitored. In one embodiment a transistor is employed as the amplifier to form a phase shift oscillator with the feedback loop coupled between the collector and base of the transistor. Transistor operating frequency is influenced by feedback loop propagation delay. The propagation delay is related to the dielectric value of the medium inside the feedback loop. Since soil moisture content is related to soil dielectric value, soil moisture content may be ascertained from the operating frequency of the oscillator. Changes in soil moisture content are calculated as a function of changes in oscillator frequency over time.

The oscillator circuit and feedback loop allow soil moisture measurement to be averaged over a relatively large area. The soil moisture measurement produced with the feedback loop is approximately an average of the soil moisture content of the soil inside the feedback loop. The area over which the soil moisture content is averaged can be modified by adjusting the size and shape of the feedback loop. Measurement averaging over a relatively large area generally produces more useful measurement data that is less susceptible to local variation in soil constitution.

The oscillator circuit and feedback loop provide accurate data without complex circuitry or the need for sophisticated calculations. Because the output of the oscillator circuit is electronic, data monitoring can be automated. In particular, the oscillator circuit and feedback loop can be implemented as a remote sensing device or as a stand-alone data logger. Simple ancillary circuitry may be employed since output is in the form of frequency. In particular, a scaling circuit and standard computer interface may be employed to obtain soil moisture measurements.

A delay line in the form of a pair of transmission wires of constant diameter that are maintained at a constant separation distance relative to one another is employed in the feedback path of a water level monitor. A first length of the transmission wire pair extending from the oscillator to the lower end of the loop is maintained in a parallel orientation relative to a second length of the transmission wire pair extending from the lower end of the loop to the oscillator. The elongated feedback loop is positioned vertically in an area where water level is to be measured, such as from the top of a well to the bottom of the well.

BRIEF DESCRIPTION OF THE DRAWING

The invention will be more fully understood from the following Detailed Description of the Invention, in conjunction with the Drawing, of which.

DETAILED DESCRIPTION OF THE INVENTION

Figure 1:
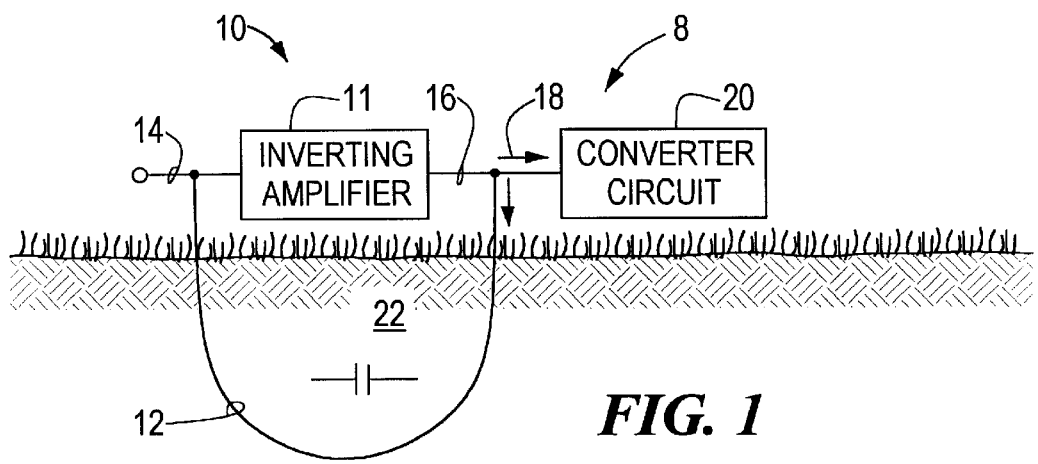
FIG. 1 is a block diagram of a soil moisture measuring device employing an oscillator circuit.

Referring to FIG. 1, a moisture and liquid level measurement device 8 includes a phase shift oscillator circuit 10 and a converter circuit 20. The oscillator circuit 10 includes an inverting amplifier 11 and a feedback loop delay line 12. The feedback loop 12 is connected between an amplifier input node 14 and an amplifier output node 16. An output signal 18 is produced by the oscillator circuit 10. The oscillator output signal 18 is applied to feedback loop 12 and the frequency to moisture content converter circuit 20. The dielectric value of the medium 22 inside the feedback loop 12 affects the propagation delay in the feedback signal applied from the output node 16 to the input node 14. The propagation delay directly affects the operation of the oscillator circuit. In particular, the propagation delay influences the operating frequency of the oscillator output signal 18. Hence, the moisture content or liquid level of medium 22 inside the feedback loop 12 can be ascertained from the frequency of the output signal 18.

The frequency to moisture content/liquid level converter circuit 20 provides an indication of moisture content or water level in response to the frequency of the output signal 18. In the illustrated embodiment the converter circuit 20 scales the frequency of the output signal 18 for simplified frequency measurement. The scaled frequency is measured and employed as an index into a translation table or other suitable device to produce a measurement in desired units.

Figure 2:
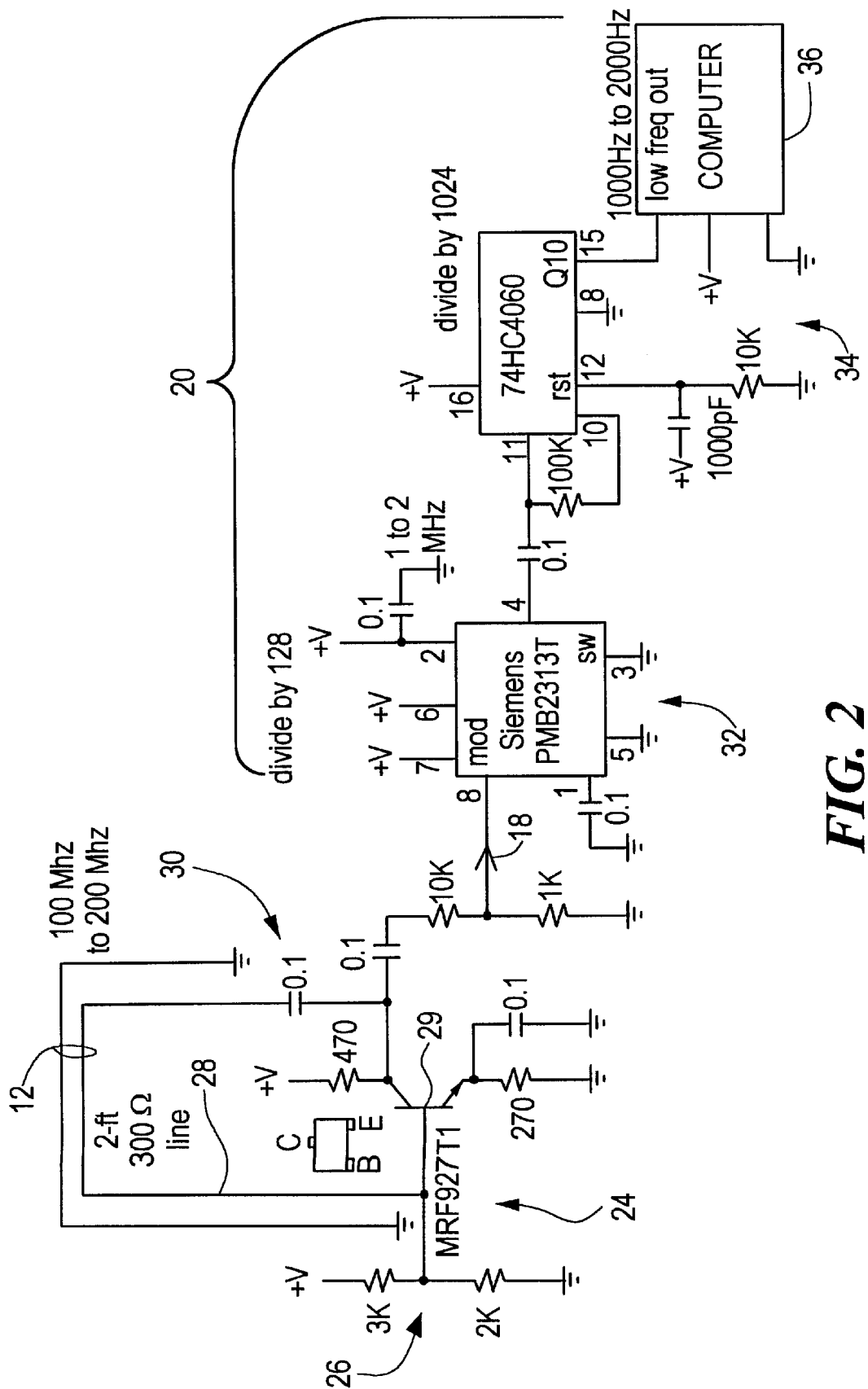
FIG. 2 is a schematic diagram of the soil measuring device of FIG. 1.

FIG. 2 is a schematic diagram of the soil moisture measuring device of FIG. 1. The illustrated embodiment provides a substantially temperature-independent output signal 18. A transistor oscillator circuit 24 is employed to provide the output signal 18. A DC voltage 26 combined with a feedback signal 28 from the transistor collector is applied to the base of the transistor 29. Propagation delay of the feedback signal 28 through the feedback loop 12 is dependent, at least in part, upon the dielectric value of the medium proximate with the feedback loop 12. In general, the greater the dielectric value of the medium, the greater the feedback propagation delay. Feedback delay influences oscillation of the transistor 29. Hence, the dielectric value of the medium inside the feedback loop can be ascertained from the frequency of the oscillator output.

In the illustrated embodiment the feedback loop 12 is approximately two feet of 300 Ω twin lead transmission wire, such as the type that is typically used for television and FM radio antenna leads. Transmission wire with a thick insulating coating is less sensitive to conditions in the surrounding medium than transmission wire with a thin coating. In the illustrated embodiment the coating provides approximately a factor of two change in frequency between air and water ($f_{air}=2*f_{water}$), as measured at the collector of the transistor 29. The operating frequency of the illustrated oscillator in an air medium is about 150 Mhz. In the illustrated configuration the transistor oscillator 24 output signal generally oscillates at a frequency between 100 MHz to 200 MHz depending upon the moisture content of the soil it is placed in. The transistor's phase shift is slightly dependent on temperature and contributes a delay equivalent to about one foot of feedback loop in air in the illustrated embodiment. The temperature dependence becomes negligible for many applications when the feedback loop is buried in soil.

The output of the transistor oscillator 24 is applied to the converter circuit 20 which reduces the frequency to one that is easily measured. The illustrated converter circuit 20 includes a high frequency prescaler circuit 32 that divides the frequency of the transistor oscillator 24 output signal 18 down to about 1 Mhz. A second divider circuit 34 operates on the output of the prescaler circuit 32 to further lower the frequency. The output of the divider circuit 34 is of sufficiently low frequency to be easily and accurately measured using a computer 36. In response to the output of the divider circuit 34 the computer 36 provides measurement data in units of soil moisture or water level. A frequency to measurement-unit conversion can be made by a conversion equation or via a predefined translation table. The table may include a plurality of frequency entries across the range of the measurement device, and a soil moisture value corresponding to each frequency entry. If the measured frequency is between two entries in the table, the nearest entry may be employed or an interpolated value may be calculated.

Figure 3:
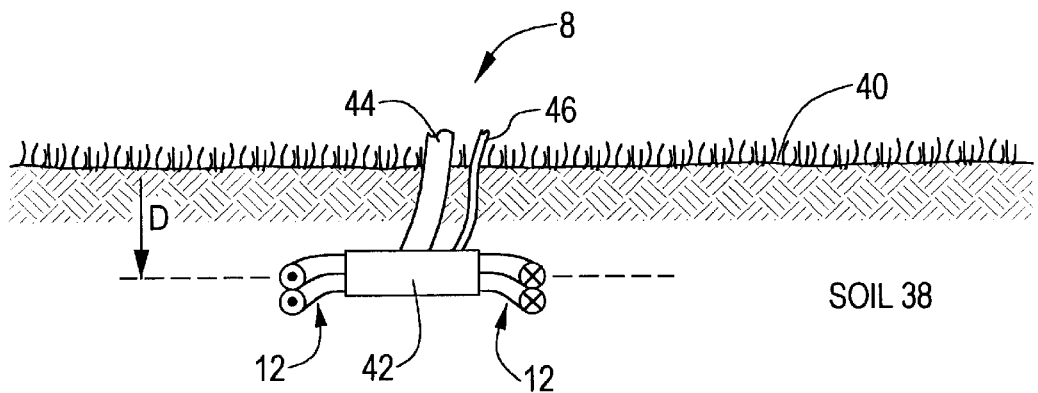
FIGS. 3 and 4 illustrate the use of the soil moisture measuring device of FIG. 1.

Referring to FIG. 3, when the medium being examined is soil 38, the illustrated measuring device is buried beneath the surface 40 of the soil 38. A protective housing or potted enclosure material 42 such as epoxy is employed to protect the internal electronics of the measurement device 8 from moisture in the soil 38. In the illustrated embodiment the measurement device 8 includes an interface that allows the feedback loop 12 to emerge from the sides of the protective housing 42.

In alternative embodiments the soil moisture measuring device 8 can be implemented as a remote sensor or as a stand-alone data logger. In the data logger configuration the measurement device is battery powered and moisture content measurements are automatically taken and stored in internal memory. A power-up reset circuit on the divider 34 (FIG. 2) allows the measurement device to be powered up only when needed, and minimizes the time needed to measure the oscillator circuit 10 (FIG. 1) frequency, thereby conserving battery power. The measurements are periodically downloaded for analysis. The download may be accomplished via a data transfer wire 44. If the data transfer wire is not employed, the download may be accomplished by removing the measurement device 8 from the soil 38. In the remote sensor configuration, soil moisture measurements are downloaded to a computer in real time via the data transfer wire 44. Further, power is supplied via a power-in wire 46, thereby eliminating reliance on battery power.

The area of soil 38 that is sampled to produce moisture content data is determined by the position, size and shape of the feedback loop 12 in the soil. The delay attributable to the feedback loop 12 is substantially determined by the dielectric value of the soil around the transmission line feedback loop 12. To measure average soil moisture content at a specific depth D below the surface 40, the feedback loop 12 is situated horizontally in a plane at a desired depth D.

Figure 4:
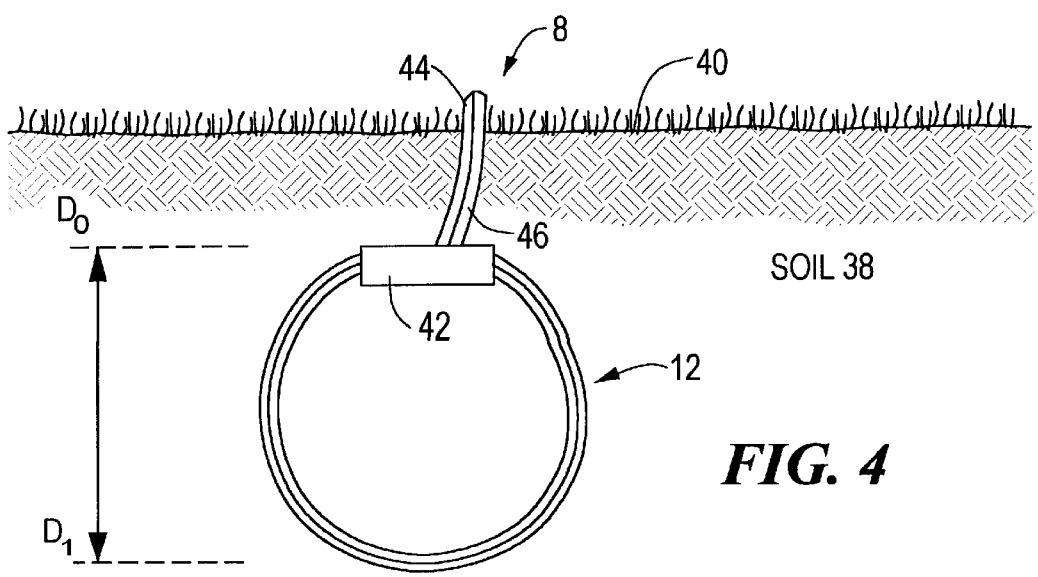

Referring now to FIG. 4, soil moisture measurements can be taken across a range of soil depths. To measure soil moisture content across a range of depths below the surface 40, e.g., from $D_0$ to $D_1$, the feedback loop 12 is situated generally vertically in the soil 38 so that it extends between depth $D_0$ and depth $D_1$. It should be noted that erroneous data may be obtained if the feedback loop 12 extends above the surface 40 of the soil 38.

Figure 5:
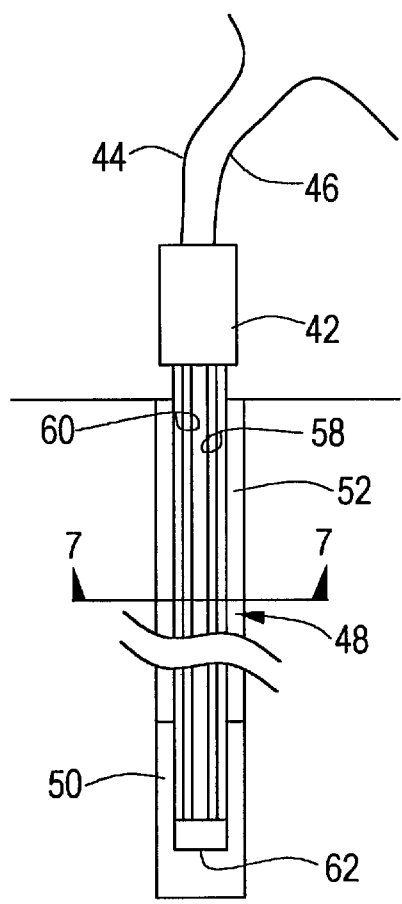
FIG. 5 is a block diagram of a water level measuring device in accordance with the present invention.
Figure 6:
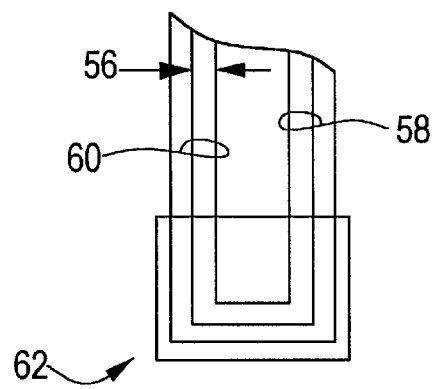
FIG. 6 further illustrates the end portion of an elongated feedback loop utilized by the measuring device of FIG. 5.
Figure 7:
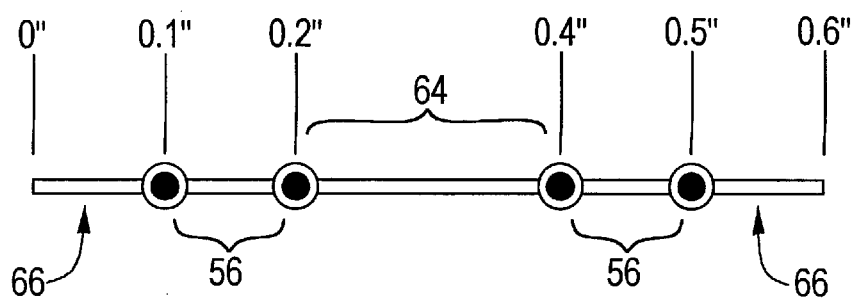
FIG. 7 is a cross sectional view of the feedback loop of FIG. 5 taken along 1—1.

In an alternative embodiment illustrated in FIGS. 5, 6 and 7 the oscillator and converter circuits are employed with an elongated feedback loop 48 to measure the level of a medium such as water 50 in an area such as a well 52. The elongated feedback loop 48 includes a pair of transmission wires that are maintained at a constant separation distance 56 relative to one another. In the illustrated embodiment the elongated feedback loop 48 is a 20 foot length (in two 10 foot portions) of 300 Ω, 30 gauge transmission wire having a separation distance 56 of 0.1 inch. A first portion 58 of the transmission wire pair that extends from the oscillator housing 42 to a lower loop end 62 is substantially parallel to a second portion 60 of the transmission wire pair extending from the lower loop end 62 to the oscillator housing 42. As shown in the cross-section view of FIG. 7, a constant separation distance 64 is maintained between the first and second loop portions 58, 60. In the illustrated embodiment the separation distance 64 is 0.2 inch. Protective strips 66 on each side of the elongated feedback loop 48 insulate the transmission wires from the walls of the well 52. The operating frequency of the illustrated oscillator/feedback loop combination in an all-air medium is approximately 10–20 MHz.

The elongated feedback loop 48 is positioned generally vertically in an area such as a well where water level is to be studied. A feedback delay that is dependent, at least in part, upon the level of water relative to the elongated feedback loop 48 is employed to calculate water level. The feedback delay is dependent upon the proportion of water to air within the elongated feedback loop 48. The operating frequency of the oscillator is dependent on the feedback delay. The dielectric value of water is different from the dielectric value of air. Consequently, water level is calculated from the operating frequency of the oscillator, with higher operating frequencies indicating higher water level. A table or other suitable device can be employed to convert the frequency measurement to a measurement in units of level and/or depth. Changes in water level are calculated as a function of changes in oscillator frequency over time.

Having described the preferred embodiments of the invention, other embodiments which incorporate concepts of the invention will now become apparent to those skilled in the art. Therefore, the invention should not be viewed as limited to the disclosed embodiments but rather should be viewed as limited only by the spirit and scope of the appended claims.

What is claimed is:

1. Apparatus for producing an indication of moisture content in a medium under observation, comprising:
    an inverting amplifier having an input and an output;
    a delay line coupled between the input and output of said amplifier to provide an oscillator producing an oscillating output signal at the output of said amplifier, wherein the output frequency of said oscillator is dependent upon the dielectric value of said medium under observation when at least a portion of said delay line is disposed within said medium; and
    a circuit responsive to said oscillator output signal frequency for producing an output signal indicative of the moisture content of said medium in the vicinity of said delay line.

2. The apparatus of claim 1 wherein said inverting amplifier includes a transistor.

3. The apparatus of claim 1 wherein the medium under observation is soil.

4. The apparatus of claim 1 wherein the delay line includes a 300 Ω twin lead transmission wire.

5. The apparatus of claim 1 wherein the frequency as measured at the amplifier output is approximately 100–200 MHz in air.

6. The apparatus of claim 1 further including a frequency reduction circuit that provides a reduced frequency signal in response to the frequency as measured at the amplifier output.

7. The apparatus of claim 6 further including a computer for providing a measurement in units of soil moisture in response to the reduced frequency signal.

8. The apparatus of claim 1 further including an internal power supply.

9. The apparatus of claim 1 further including an internal memory for storing moisture content measurements.

10. The apparatus of claim 1 further including an external power supply.

11. The apparatus of claim 1 further including an external data connection for transmitting moisture content measurements.

12. The apparatus of claim 3 wherein the delay line is disposed horizontally in the soil in a plane at a depth D below the surface.

13. The apparatus of claim 3 wherein the delay line is disposed vertically in the soil in a plane ranging from a depth $D_0$ to a depth $D_1$.

14. A method for producing an indication of moisture content in a medium under observation using a phase shift oscillator circuit having an input and an output and a feedback loop coupled between the phase shift oscillator input and output, comprising the steps of:
    positioning the delay line in the medium;
    monitoring frequency as measured at the phase shift oscillator circuit output; and
    producing an output signal indicative of the moisture content of the medium in the vicinity of the delay line from the monitored frequency of the phase shift oscillator circuit.

15. The method of claim 14 including the further step of providing a reduced frequency signal from the phase shift oscillator circuit output with a frequency reduction circuit.

16. The method of claim 15 including the further step of providing a measurement in units of soil moisture in response to the frequency signal provided by the frequency reduction circuit.

17. The method of claim 14 including the further step of situating the delay line horizontally in soil in a plane at a depth D below the surface.

18. The method of claim 14 including the further step of situating the delay line vertically in the soil in a plane ranging from a depth $D_0$ to a depth $D_1$.

19. A device for producing an indication of level of a liquid in an area under observation, comprising:

an inverting amplifier having an input and an output;

a delay line coupled between the input and output of said amplifier to provide an oscillator producing an oscillating output signal at the output of said amplifier, wherein the frequency of said oscillator is dependent upon the dielectric value of said medium under observation when at least a portion of said delay line is disposed within said medium; and a circuit responsive to said oscillator output signal frequency for producing an output signal indicative of the liquid level in the vicinity of said delay line.

20. The apparatus of claim 19 wherein the inverting amplifier includes a transistor.

21. The apparatus of claim 19 wherein the delay line includes first and second elongated parallel portions that are coupled at a distal end of the first and second portions relative to the amplifier.

22. The apparatus of claim 19 wherein the delay line includes a 300 Ω twin lead transmission wire.

23. The apparatus of claim 19 wherein the frequency as measured at the amplifier output is approximately 10–20 MHz in air.

24. The apparatus of claim 19 further including a frequency reduction circuit that provides a reduced frequency signal in response to the frequency as measured at the amplifier output.

25. The apparatus of claim 24 further including an internal power supply.

26. The apparatus of claim 19 further including an internal memory for storing liquid level measurements.

27. The apparatus of claim 19 further including an external power supply.

28. The apparatus of claim 19 further including an external data connection for transmitting liquid level measurements.

29. A method for producing an indication of the level of a liquid in a region under observation using a phase shift oscillator circuit having an input and an output and a feedback loop coupled between the phase shift oscillator input and output, comprising the steps of:

positioning the delay line in the region;

monitoring frequency as measured at the phase shift oscillator circuit output; and producing an output signal indicative of the liquid level in the vicinity of the delay line from the monitored frequency of the phase shift oscillator circuit.

30. The method of claim 29 including the further step of scaling the phase shift oscillator circuit output with a frequency reduction circuit to provide a reduced frequency signal.

31. The method of claim 30 including the further step of providing a measurement in units of liquid level in response to the frequency signal provided by the frequency reduction circuit.

* * * * *